United States Patent [19]

Kitamura

[11] Patent Number: 4,840,630
[45] Date of Patent: Jun. 20, 1989

[54] ARTIFICIAL HIP JOINT

[75] Inventor: Yasuhiro Kitamura, Kyoto, Japan

[73] Assignee: Kyocera Corporation, Kyoto, Japan

[21] Appl. No.: 154,504

[22] Filed: Feb. 4, 1988

Related U.S. Application Data

[63] Continuation of Ser. No. 873,288, Jun. 5, 1986, abandoned, which is a continuation of Ser. No. 592,605, Mar. 22, 1984, abandoned.

[51] Int. Cl.$^4$ ............................................. A01F 2/34
[52] U.S. Cl. ..................................................... 623/22
[58] Field of Search ...................... 623/16, 18, 20, 22, 623/23

[56] References Cited

U.S. PATENT DOCUMENTS

| | | | |
|---|---|---|---|
| 4,051,559 | 10/1977 | Pifferi | 623/22 |
| 4,184,213 | 1/1980 | Helmke | 623/23 |
| 4,205,400 | 6/1980 | Shen et al. | 623/20 |
| 4,217,666 | 8/1980 | Averill | 623/20 |
| 4,234,972 | 11/1980 | Hench et al. | 623/16 |
| 4,285,070 | 8/1981 | Averill | 623/20 |
| 4,666,450 | 5/1987 | Kenna | 623/22 |

FOREIGN PATENT DOCUMENTS

| | | | |
|---|---|---|---|
| 0010527 | 4/1980 | European Pat. Off. | 623/22 |
| 0053794 | 6/1982 | European Pat. Off. | 623/22 |
| 2349357 | 4/1975 | Fed. Rep. of Germany | 623/22 |
| 2411617 | 4/1975 | Fed. Rep. of Germany | 623/22 |
| 2751537 | 5/1979 | Fed. Rep. of Germany | 623/22 |
| 2805868 | 8/1979 | Fed. Rep. of Germany | 623/18 |
| 2395011 | 2/1979 | France | 623/22 |
| 572335 | 2/1976 | Switzerland | 623/18 |

*Primary Examiner*—V. Millin
*Assistant Examiner*—David J. Isabella
*Attorney, Agent, or Firm*—Spensley Horn Jubas & Lubitz

[57] ABSTRACT

An artificial hip joint for connecting a hipbone with a thighbone is disclosed. Its external frame member to be secured in the hipbone, at least the section directly contacting the hipbone, is made of ceramic material, and a socket plug for rotatably supporting the condyle of a stem member is made of plastic material.

3 Claims, 1 Drawing Sheet

ARTIFICIAL HIP JOINT

This is a continuation of application Ser. No. 06/873,288 filed on June 5, 1986, now abandoned, which in turn is a continuation of application Ser. No. 06/592,605 filed on Mar. 22, 1984, now abandoned.

BACKGROUND OF THE INVENTION

1. Field of the Invention

This invention relates to an artificial hip joint for artificially remedying the hip joint of a living body and for restoring the function and form of the hip joint 2. Prior Art When the function of a hip joint is damaged due to an external injury caused by a traffic accident or degeneration of the hip joint bone caused by rheumatism or a tumor, and is difficult to be recovered, the hip joint is generally cut off and replaced with an artificial hip joint.

The artificial hip joint used for the above-mentioned purpose should meet the following requirements: (1) The hip joint must have superior affinity to its surrounding tissue since it is embedded in a living body for an extended period. (2) The hip joint must not be degenerated in the living body, and its characteristics, such as mechanical strength, must remain unchanged. (3) The sliding section of the hip joint must exhibit superior wear resistance during swinging and be capable of performing the basic joint function. Particularly, the section to be embedded in the bone must be strong and the sliding section must have superior impact strength. It has been ascertained that several times as heavy as the living body may be applied to the hip joint when the corresponding muscle is activated and the weight of the living body is applied. Accordingly, the artificial hip joint must have great mechanical strength and its members must be securely connected with the bone of the living body. Many artificial hip joint meeting these requirements have been developed with due regard to combination of materials. More specifically, an alloy steel with high mechanical strength and high corrosion resistance is usually used for the stem of an artificial hip joint, which is embedded in a thighbone. Table 1 shows known combinations of materials for the condyle which is located at the end of the stem and materials for the socket which swingably accommodates the condyle and is embedded and secured in the hipbone.

TABLE 1

| Combination | Material | |
|---|---|---|
| example | Condyle | Socket |
| No. 1 | Metal | Metal |
| No. 2 | Plastics | Metal |
| No. 3 | Metal | Plastics |
| No. 4 | Ceramics | Ceramics |
| No. 5 | Ceramics | Plastics |

The artificial hip joint which is made of the materials of combination example No. 1 (metal-metal) has high mechanical strength. However, when the condyle slides (swings) in the socket, metal particles are generated and dissolve into body fluids as metal ions. The metal ions are harmful to the living body and damage the tissue around the hip joint. Therefore, the combination is not suited for use for an extended period. At present, artificial hip joint made of a metal condyle and a metal socket are scarcely used. The artificial hip joint which is made of the materials of combination example No. 4 (ceramics-ceramics) does not cause harm to the living body. However, when an impact load, several times as heavy as the body, is applied to the contact position of the two ceramic elements with a Vickers hardness of 1800, the ceramic elements may frequently break since they cannot dampen impacts and ceramic material is not tough but brittle. This is a grave defect of the artificial hip joint made of ceramic material (combination example No. 4), although its ceramic socket can be directly embedded in and connected to the bone since it is harmless and has superior affinity to the living body.

The artificial hip joint which is made of a plastic socket and a metal or ceramic condyle (combination example No. 3 or No. 5) shows superior impact damping performance since a relatively soft plastic sliding surface contacts a hard metal or ceramic material. Furthermore, particles due to friction are scarcely generated since the socket made of plastic material, such as polyethylene and polypropylene, has superior sliding performance and flexibility. Moreover, the plastic socket is almost harmless to the living body. Therefore, the artificial hip joint (combination example No. 3 or No. 5) is good for practical use. However, the plastic socket has poor affinity to the living body, although it is almost harmless. Accordingly, the socket must be securely attached to the bone using methyl meta-acrylate (bone cement) so that the socket can be embedded and secured in the hipbone. When the bone cement cures, solidification heat of 60°–80° C. generates and damages the surrounding tissue. Even after curing, polymerization proceeds. As time passes, the cement becomes brittle and is prone to disintegrate, thus it loses its effect. As a result, the artificial hip joint may not function as intended, although the hip joint itself is not damaged at all. Furthermore, residual monomer, which is not yet reacted, gradually dissolves and adversely affects metabolism of the bone. Thus the bone contacting the bone cement is absorbed and the connection strength between the socket and the bone decreased as time passes. This fatal defect has not yet been remedied.

SUMMARY OF THE INVENTION

It is therefore the principal object of the present invention to provide an artificial hip joint which can be securely connected with a living bone for an extended period by fully utilizing the advantages of plastic and ceramic materials and the superior combination of the two materials.

The object will become more apparent when a preferred embodiment of the present invention is considered in connection with the drawings.

BRIEF DESCRIPTION OF THE DRAWINGS

FIG. 1 shows as embodiment of the artificial hip joint of the present invention. A hipbone B1 is swingably connected with a thighbone B2 via the artificial hip joint. The artificial hip joint is composed of a stem M which is made of stainless steel for example and is embedded in the thighbone B2 and a socket S which is embedded in the hipbone B1.

A condyle K which is made of smoothly finished metal or single-crystal alumina ceramics (sapphire) or poly-crystal alumina ceramics is provided at one end of the metal stem M. The condyle K is rotatably or swingably fit in and connected with the spherical concave section F in the socket S which is securely embedded in the hipbone B1. FIG. 2 is an enlarged sectional view of the socket S of the artificial hip joint used to connect the hipbone B1 with the thighbone B2. The socket is embedded in the pelvis (hipbone) of the living body. An external member C contacting the hipbone B1 is made of alumina or other ceramic material with high mechanical strength and is equipped with a thread groove Ca around its external circumference so that the socket can be screwed and secured in the living body and the joining force of the socket can be increased by allowing the bone to penetrate and propagate into the thread groove. A flange section Cb is integrated around the circumference of the external frame member C for convenience so that the embedding position of the socket can be easily determined and the load to the socket S can be stably received. A plastic socket plug P is secured in the almost hemispheric concave section D of the ceramic external frame member C. The socket plug P is made of polyethylene for example, more specifically injection-molded high-density polyethylene. It is fit and secured in the concave section D. The load receiving surface of the socket plug P has a spheric concave section F so that the condyle can be smoothly slid therein. In the case of this example, plural undercut-tooth-shaped concave sections Cc are provided on the hemispheric concave section D of the ceramic external frame member C. The plastic socket plug P are pressure-fit in the concave section Cc, thus undercut sections Pa are formed on the plug. These undercut sections prevent the plastic socket plug P from separating from the external frame member C or rotating. They also function to compensate for the thermal expansion difference between the plastic socket plug P and the external frame member C.

Figure 1:
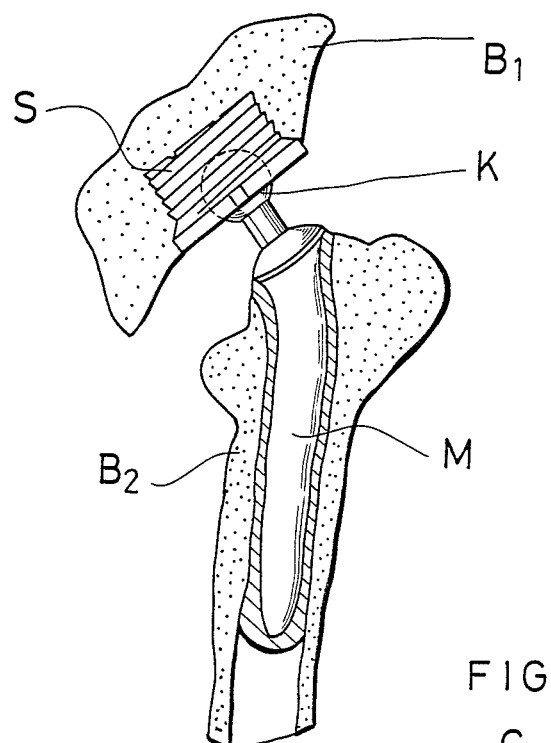
FIG. 1 shows the artificial hip joint of a preferred embodiment of the present invention, which is embedded in a living bone.
Figure 2:
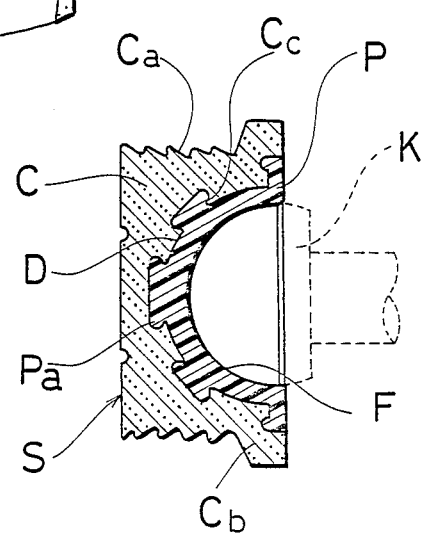
FIG. 2 is an enlarged vertical sectional view of the socket member of the artificial hip joint.

Instead of making the entire external frame member C out of ceramic material, it can be made of metal except that at least the section being embedded in and contacting the living tissue can be coated with a layer of ceramic material, such as alumina ceramics, zirconia ceramics or apatite ceramics, which has good affinity to the living tissue, by injection or other means. In addition, the plastic socket plug P can be connected with the concave section of the external frame member C by injection forming, pressure fitting or screw tightening. Accordingly, with the artificial hip joint of the present invention constructed as described above, when the socket S is secured in the hipbone B1, the external frame member C made of alumina ceramics for example contacts the living bone and the external frame member C is firmly connected with the hipbone B1 as the bone proliferates. This is possible because the alumina ceramics for the external frame member C or the coated layer of ceramic material, such as alumina ceramics or apatite ceramics, over the external circumference of the external frame member made of metal has extremely superior affinity to the living bone and is harmless to the living body. Therefore, the connection can be maintained stably for an extended period.

Furthermore, superior sliding performance and connection are assured for an extended period at the connection between the spheric concave section F which is formed at the almost central position of the plastic socket plug P secured in the external frame member C firmly connected to the living body and the condyle K which is accommodated in the spheric concave section F because the high impact resistance and superior sliding performance of the socket plug P are well combined with the high wear resistance of the ceramic or metal material of the smooth-finished condyle K.

As described above, the socket of the artificial hip joint of the present invention, at least the section directly contacting the living body, is made of or coated with ceramic material, such as alumina ceramics, zirconia ceramics or apatite ceramics, which has high mechanical strength and superior affinity to the living tissue and is harmless to the living body. As a result, it is not necessary to use the bone cement, which is harmful to the living body, to embed and secure the socket of the artificial hip joint. Moreover, the sliding surface contacting the smooth-finished condyle is made of plastic material, such as polyethylene, which has superior sliding performance and is best suited for the socket. Consequently, the artificial hip joint of the present invention has sufficient mechanical strength, high performance and high durability, and can be made at a lower cost. Therefore, the artificial hip joint of the present invention will be able to greatly improve the welfare of mankind.

Although the invention has been described in its preferred form with a certain degree of particularity, it is understood that the present disclosure of the preferred form has been changed in the details of construction and the combination and arrangement of parts may be restored to without departing from the spirit and the scope of the invention as hereinafter claimed.

We claim:
1. An artificial hip joint comprising:
a socket member having a ceramic external frame member to be secured in a hipbone and a cup-shaped, high-density molded polyethylene socket plug held and secured in said external frame member; and
a stem member having a condyle portion at a first end thereof and a second, opposite end thereof designed to be embedded and secured in a thigh bone, wherein said socket plug rotatably supports a spherical section of said condyle portion, and has a plurality of undercut protrusions,
wherein said external frame member has a generally concave section having a plurality of sockets defined therein, the protrusions of said socket plug being disposed in said sockets, thereby securely joining the socket plug to the external ceramic frame member so as to preclude movement of the socket plug relative to the ceramic frame, the undercut protrusions serving to compensate for the thermal expansion coefficient difference between the socket plug and the external frame member;
said ceramic frame member consisting essentially of a ceramic selected from the group consisting of alumina ceramics, zirconia ceramics and apatite ceramics; and
said condyle portion consisting essentially of monocrystalline alumina ceramics or polycrystalline zirconia ceramics.
2. An artificial hip joint comprising:
a socket member to be secured in a hip bone, the socket member having a threaded external frame member with a flange on the external circumference thereof, wherein at least external surfaces thereof contacting the hip bone consist essentially of a ceramic selected from the group consisting of alumina ceramics, zirconia ceramics and apatite ceramics, and a cup-shaped high density molded polyethylene socket plug held and secured in the external frame member; and a stem member having a condyle portion at a first end thereof and a second, opposite end being designed for insertion into a thigh bone, wherein said socket plug rotatably supports a spherical section of said condyle portion, wherein the socket plug and external frame member include a plurality of alternating undercut tooth-shaped concave protrusions and opposing pockets located on their mutually contacting surfaces for mating engagement of the protrusions of one member with the pockets of the other, thereby securely joining the socket plug to the external frame member so as to preclude movement of the socket plug relative to the external frame member, the undercut protrusions serving to compensate for the thermal expansion coefficient difference between the socket plug and the external frame member;

said condyle portion consisting essentially of monocrystalline alumina ceramics or polycrystalline zirconia ceramics.

3. The artificial hip joint of claim 2 wherein the socket member consists essentially of a ceramic selected from the group consisting of alumina ceramics, zirconia ceramics and apatite ceramics.

* * * * *